(12) United States Patent
Sati

(10) Patent No.: US 11,127,494 B2
(45) Date of Patent: Sep. 21, 2021

(54) CONTEXT-SPECIFIC VOCABULARY SELECTION FOR IMAGE REPORTING

(71) Applicant: INTERNATIONAL BUSINESS MACHINES CORPORATION, Armonk, NY (US)

(72) Inventor: Marwan Sati, Mississauga (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 700 days.

(21) Appl. No.: 15/244,584

(22) Filed: Aug. 23, 2016

(65) Prior Publication Data

US 2017/0061100 A1   Mar. 2, 2017

Related U.S. Application Data

(60) Provisional application No. 62/210,248, filed on Aug. 26, 2015.

(51) Int. Cl.
```
G06F 40/00      (2020.01)
G16H 30/40      (2018.01)
G10L 15/183     (2013.01)
G06F 16/2452    (2019.01)
G06F 16/2457    (2019.01)
G16H 15/00      (2018.01)
```
(Continued)

(52) U.S. Cl.
CPC ....... *G16H 30/40* (2018.01); *G06F 16/24522* (2019.01); *G06F 16/24575* (2019.01); *G06F 40/30* (2020.01); *G10L 15/183* (2013.01); *G10L 15/26* (2013.01); *G16H 15/00* (2018.01); *G16H 30/00* (2018.01); *G16H 30/20* (2018.01); *G06F 40/242* (2020.01); *G06F 40/284* (2020.01); *G10L 15/18* (2013.01); *G10L 15/22* (2013.01)

(58) Field of Classification Search
CPC combination set(s) only.
See application file for complete search history.

(56) References Cited

U.S. PATENT DOCUMENTS

| 9,014,485 B2 | 4/2015 | Moehrle |
| 2002/0131625 A1 | 9/2002 | Vining et al. |

(Continued)

OTHER PUBLICATIONS

Non-Final Office Action from the U.S. Patent and Trademark Office for U.S. Appl. No. 15/244,565 dated Aug. 25, 2020 (22 pages).

(Continued)

*Primary Examiner* — Vu B Hang
(74) *Attorney, Agent, or Firm* — Michael Best & Friedrich LLP

(57) ABSTRACT

Methods and systems for using contextual information to generate reports for image studies. One method includes determining contextual information associated with an image study wherein at least one image included in the image study loaded in a reporting application. The method also includes automatically selecting, with an electronic processor, a vocabulary for a natural language processing engine based on the contextual information. In addition, the method includes receiving, from a microphone, audio data and processing the audio data with the natural language processing engine using the vocabulary to generate data for a report for the image study generated using the reporting application.

15 Claims, 2 Drawing Sheets

(51) Int. Cl.
    *G10L 15/26*      (2006.01)
    *G16H 30/00*      (2018.01)
    *G16H 30/20*      (2018.01)
    *G06F 40/30*      (2020.01)
    *G06F 40/242*     (2020.01)
    *G10L 15/22*      (2006.01)
    *G06F 40/284*     (2020.01)
    *G10L 15/18*      (2013.01)

(56)          References Cited

U.S. PATENT DOCUMENTS

| 2008/0103828 | A1  | 5/2008  | Squilla et al. |
| 2014/0344701 | A1* | 11/2014 | Shreiber ............. G06F 3/04842 |
|              |     |         | 715/728 |
| 2014/0379364 | A1  | 12/2014 | Liu et al. |
| 2015/0019537 | A1  | 1/2015  | Neels et al. |
| 2015/0169052 | A1* | 6/2015  | Kramer ................. G06F 3/013 |
|              |     |         | 345/156 |
| 2016/0012319 | A1  | 1/2016  | Mabotuwana et al. |

OTHER PUBLICATIONS

Non-Final Office Action from the U.S. Patent and Trademark Office for U.S. Appl. No. 15/244,565 dated Nov. 29, 2019 (19 pages).
Final Office Action from the U.S. Patent and Trademark Office for U.S. Appl. No. 15/244,565 dated Mar. 3, 2021 (26 pages).
MRS7 Reporting <http://mrsys.com/products/mrs7-reporting/> dated Jan. 6, 2014, as found on the WayBackMachine.

* cited by examiner

CONTEXT-SPECIFIC VOCABULARY SELECTION FOR IMAGE REPORTING

BACKGROUND

Embodiments of the invention provide methods and systems for using contextual information within a reporting software application to generate a report, such as a structured report, for an image study.

SUMMARY

A reviewing physician (a "reviewer") generates a report as part of an image study (e.g., a cardiology report, ultrasound report, etc.). A reviewer may dictate the report and a natural language processing engine may attempt to understand the words and semantics of free speech to determine discrete data elements for the report. Although this approach is easy to use from the perspective of the reviewer, the resulting report is unstructured, which makes data mining and other analytics difficult. Also, certain clinical areas lexicons contain specific terms and an expected report structure that cannot be created efficiently through free speed recognition. Furthermore, some types of reports (e.g., cardiology) are too complex or too lengthy to be properly handled through a natural language processing engine.

Alternatively, structured reporting software applications allow a reviewer to generate a structured report. For example, a structured reporting software application may provide a menu of available report data elements that a reviewer may select and then populate the applicable data elements (e.g., provide values for the selected data elements). The menu of available data elements is commonly structured as a tree structure, where a user may drill-down from a high-level report type to specific data elements. Using such a tree structure, however, requires a reviewer to select discrete data elements that are used to form written sentences included in a final report, which involves a large amount of user interaction with the software application (e.g., mouse clicks) that may interrupt the reviewer from viewing data (e.g., images) that he or she is reporting on. However, the resulting structured report includes discrete data elements that are clearly defined, which enables powerful analytics.

Embodiments of the invention provide methods and systems for using contextual information within a reporting application, such as a medical software reporting application, to generate a report. For example, one method may include automatically selecting a vocabulary for a natural language processing engine based on contextual information available to the reporting application and using the selected vocabulary to process free speech (e.g., spoken or written) representing a report or discrete data elements thereof. Another method may include automatically selecting one or more discrete data elements for a structured report based on contextual information available to the reporting application and displaying the selected one or more discrete data elements to a reviewer. In some embodiments, the reviewer may select one of the displayed data elements for inclusion in a structured report.

For example, one embodiment provides a method of generating reports for image studies. The method includes determining contextual information associated with an image study, at least one image included in the image study loaded within a reporting application and automatically selecting, with an electronic processor, at least one discrete data element for a structured report generated using the reporting application for the image study based on the contextual information. The method also includes receiving a value for the at least one discrete data element and adding the value for the at least one discrete data element to the structured report.

Another embodiment provides a system for generating a structured report for data. The system includes an electronic processor configured to determine contextual information associated with the data, and automatically select at least one discrete data element for a structured report generated using the reporting application for the data based on the contextual information. The electronic processor is also configured to receive a value for the at least one discrete data element, and add the value for the at least one discrete data element to the structured report.

An additional embodiment provides non-transitory computer-readable medium that includes instructions that, when executed by an electronic processor, perform a set of functions. The set of functions includes determining contextual information associated with at least one image and automatically selecting at least one discrete data element for a structured report generated using a reporting application for the image study based on the contextual information. The set of functions also includes receiving a value for the at least one discrete data element and adding the value for the at least one discrete data element to the structured report within the reporting application.

Yet another embodiment provides a method of generating reports for image studies. The method includes determining contextual information associated with an image study, wherein at least one image included in the image study loaded in a reporting application. The method also includes automatically selecting, with an electronic processor, a vocabulary for a natural language processing engine based on the contextual information. In addition, the method includes receiving, from a microphone, audio data and processing the audio data with the natural language processing engine using the vocabulary to generate data for a report for the image study generated using the reporting application.

Another embodiment provides a system for generating a structured report for data. The system includes an electronic processor. The electronic processor is configured to determine contextual information associated with the data, automatically select a vocabulary for a natural language processing engine based on the contextual information, receive audio data from a microphone, and process the audio data with the natural language processing engine using the vocabulary to generate the structured report for the data.

A further embodiment provides non-transitory computer-readable medium including instructions that, when executed by an electronic processor, perform a set of functions. The set of functions includes determining contextual information associated with at least one image loaded in a reporting application and automatically selecting a vocabulary for a natural language processing engine based on the contextual information. The set of functions also includes receiving audio data and processing the audio data with the natural language processing engine using the vocabulary to generate data for a report for the at least one image generated using the reporting application.

DETAILED DESCRIPTION

Figure 1:
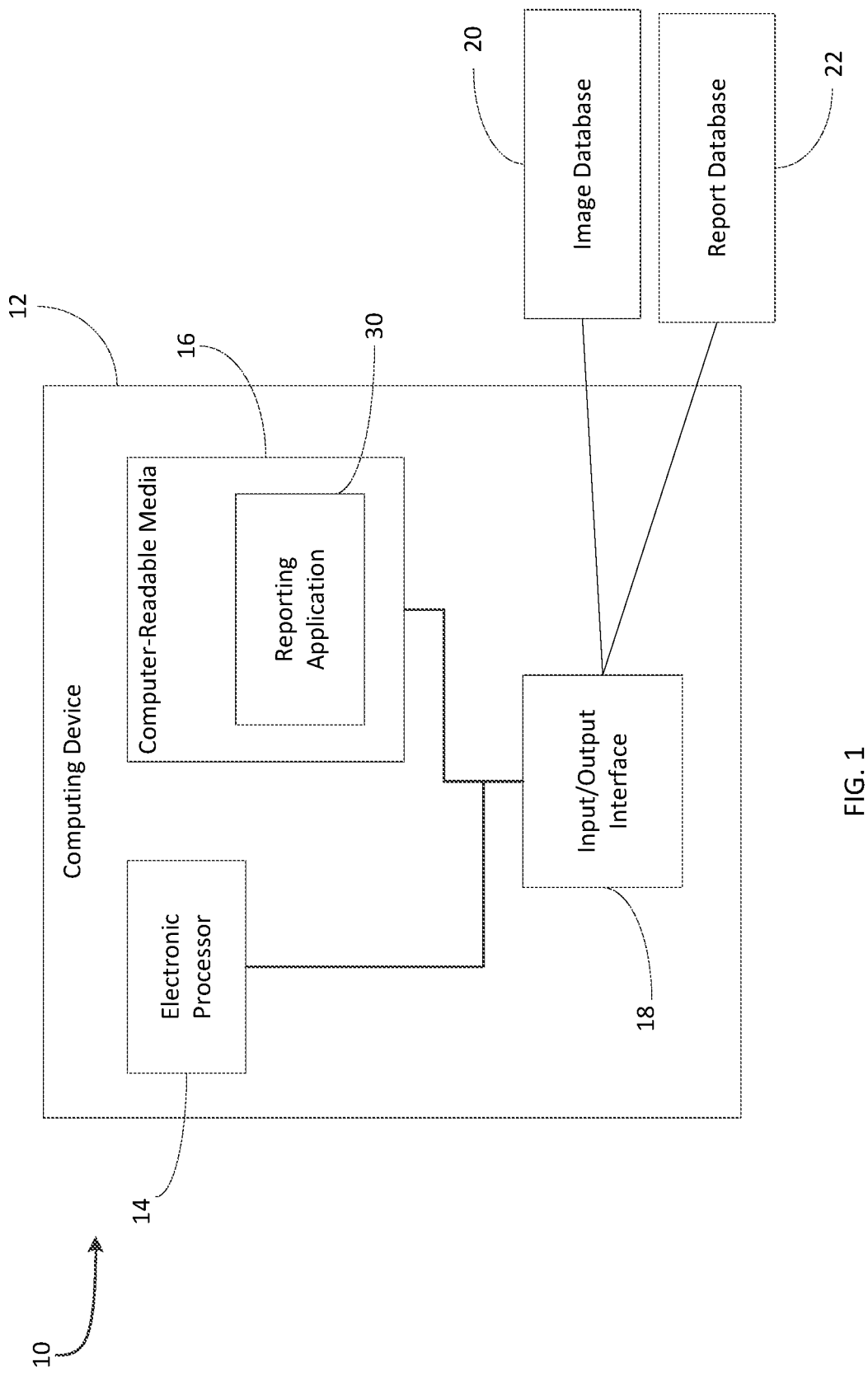
FIG. 1 schematically illustrates a system for generating a report.

FIG. 1 schematically illustrates a system 10 for generating a report for an image study. It should be understood that FIG. 1 illustrates only one example of a system 10 for generating a report and that other configurations are possible. As shown in FIG. 1, the system 10 includes a computing device 12 that includes an electronic processor 14, non-transitory computer-readable media 16, and an input/output interface 18. Although the electronic processor 14, the computer-readable media 16, and the input/output interface 18 are illustrated as part of a single computing device 12 (e.g., such as a personal computer or a server), the components of the computing device 12 may be distributed over multiple computing devices 12. Similarly, the computing device 12 may include multiple electronic processors, computer-readable media modules, and input/output interfaces and may include additional components than those illustrated in FIG. 1.

The electronic processor 14 retrieves and executes instructions stored in the computer-readable media 16. The electronic processor 14 may also store data to the computer-readable media 16. The computer-readable media 16 may include non-transitory computer readable media and may include volatile memory, non-volatile memory, or combinations thereof. In some embodiments, the computer-readable media 16 includes a disk drive or other type of large capacity storage mechanism.

The input/output interface 18 receives information from sources external to the computing device 12 and outputs information from the computing device 12 to external sources. For example, the input/output interface 18 may include a network interface, such as an Ethernet card or a wireless network card, that allows the computing device 12 to send and receive information over a network, such as a local area network or the Internet. In particular, as illustrated in FIG. 1, in some embodiments, the input/output interface 18 communicates with an image database 20 and a report database 22 over a wired or wireless connection or network. The image database 20 may store patient information, including images, patient identifiers, patient history, order information, and the like. The report database 22 stores reports, such as structured image study reports. In some embodiments, the image database 20 and the report database 22 are combined in a single database. In other embodiments, the image database 20 and/or the report database 22 are distributed over multiple databases. Also, in some embodiments, the image database 20 and/or the report database 22 is included within the computing device 12 (e.g., as part of the computer-readable media 16).

In some embodiments, the computing device 12 may also include one or more wired or wireless ports and associated drivers to receive and send data to and from one or more peripheral devices, such as a keyboard, a microphone, a mouse, a printer, a monitor, etc., communicating with the computing device 12.

The instructions stored in the computer-readable media 16 perform particular functionality when executed by the electronic processor 14. For example, as illustrated in FIG. 1, the computer-readable media 16 includes a reporting application 30. As described in more detail below, the reporting application 30, when executed by the electronic processor 14, generates reports, such as structured reports for medical image studies (e.g., cardiology reports, ultrasound reports, and the like). The reporting application 30 may include a software application that provides reporting alone or in combination with other functions (e.g., a combined medical software application). For example, the reporting application 30 may provide imaging and reporting, viewing and reporting (e.g., pathology viewing and reporting systems or EKG viewing and reporting systems), and the like.

In some embodiments, the computing device 12 is a personal computer operated by a reviewer to locally store and execute the reporting application 30. However, in other embodiments, the computing device 12 is a server that hosts the reporting application 30 as a network-based application. Therefore, a reviewer may access the reporting application 30 through a communication network, such as the Internet. Accordingly, in some embodiments, a reviewer is not required to have the reporting application 30 installed on their workstation or personal computer. Rather, the reviewer may access the reporting application 30 using a browser application, such as Internet Explorer® or FireFox®.

The reporting application 30 interacts with the image database 20 to access images, generates a report based on the images (e.g., based on input from a reviewer), and stores the generated report to the report database 22. In some embodiments, the image database 20 and/or the report database 22 are included in a picture archiving and communication system ("PACS"). Also, in some embodiments, the computing device 12 is included in a PACS. In other embodiments, the computing device 12 may access the image database 20, the report database 22, and other components of a PACS through the input/output interface 18.

As noted above, the reporting application 30 allows a reviewer to generate a report for an image study (e.g., a set of images associated with a patient). In some embodiments, the reporting application 30 allows a user to dictate a report using free speech, which the reporting application 30 translates into text using a natural language processing engine. However, as noted above, this type of report is often difficult to analyze given its unstructured format. Accordingly, alternatively or in addition, the reporting application 30 may allow a user to build a report using discrete data elements that the user selects through a data structure, such as a tree-structure (e.g., individually or as subsets). This approach results in a structured report but increases the time required and interaction required from the reviewer to generate the report.

Figure 2:
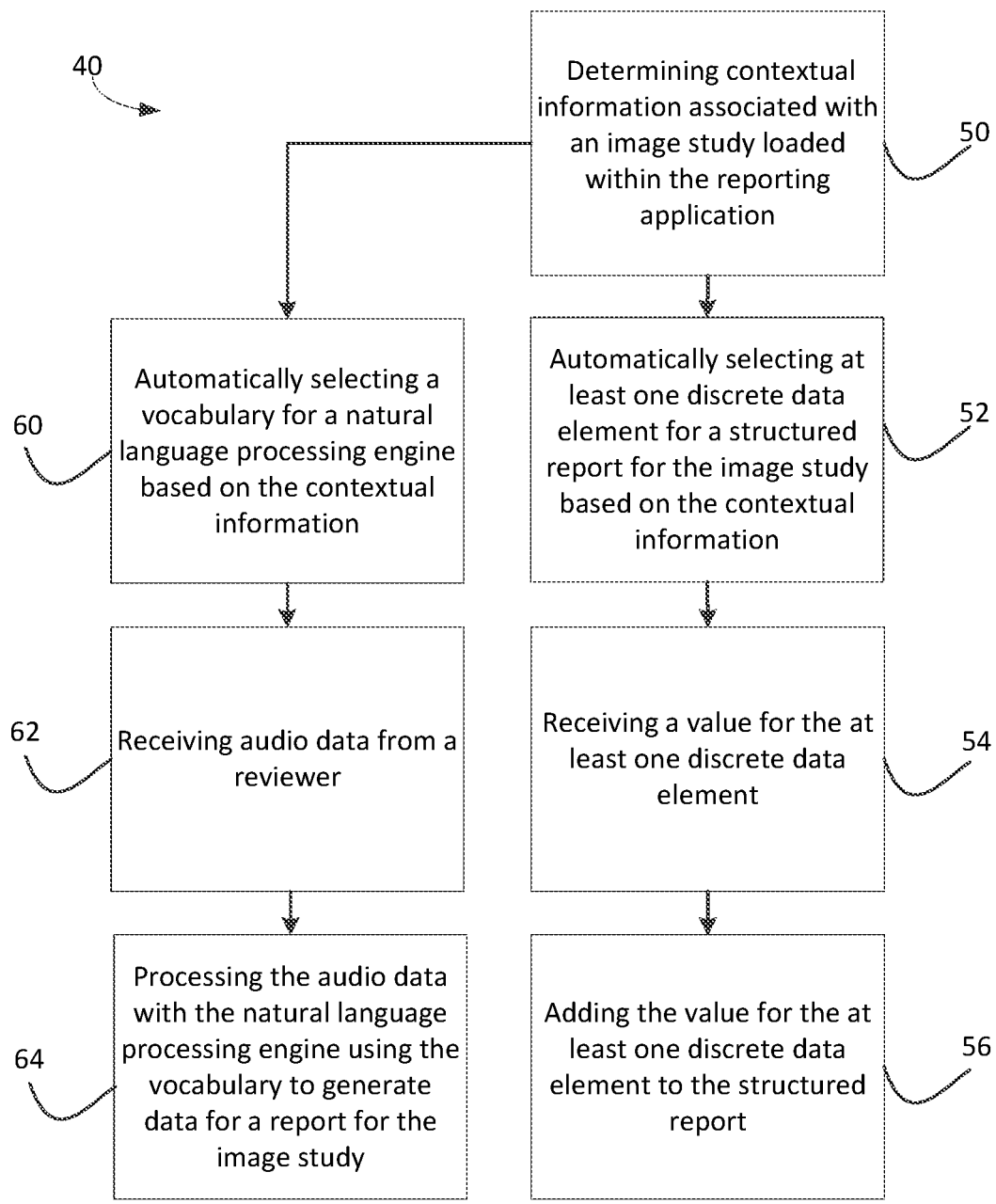
FIG. 2 is a flow chart illustrating a method performed using the system of FIG. 1 to generate for a report based on contextual information.

Accordingly, to solve these and other problems associated with existing reporting applications, FIG. 2 illustrates a method 40 performed by the system 10 for generating a report for an image study based on contextual information. The method 40 is described below as being performed by the reporting application 30 (e.g., as executed by the electronic processor 14). However, the method 40 or portions thereof may be performed by one or more separate software applications that interact with the reporting application 30 (e.g., as add-on functionality).

As illustrated in FIG. 2, the method 40 includes determining contextual information associated with an image study, at least a portion of which (e.g., at least one image) is loaded (e.g., selected, opened, displayed, etc.) within the reporting application 30 (at block 50). The contextual information may include information available from one or more images included in the image study (e.g., obtained from the image database 20), such as an image type (e.g., a computed tomography image, an ultrasound image, or the like), a number of images included in the image study, a portion of an image or a particular image within a series of images currently being displayed within the reporting application 30, Digital Imaging and Communications in Medicine ("DICOM") header information (e.g., gender information, age information, exam information, and the like), the hanging protocol associated with the image study (i.e., a set of actions used to arrange images for viewing), or a combination thereof. Similarly, in some embodiments, the contextual information includes anatomy information (e.g., an anatomical structure represented in the medical image), which may be pulled from image header information or may be automatically identified based on one or more images included in the image study using image analytics.

Alternatively or in addition, the contextual information may include patient information associated with images being reported on within the reporting application 30. For example, the reporting application 30 may be configured to use information contained in the displayed images (e.g., a patient identifier included in header information) to access a patient's medical history, which may be stored in the image database 20 or a separate database internal or external to the computing device 12. The patient information may include exams and reports related to the image study, such as electrophysiology reports and vascular reports, and annotations (e.g., notes, measurements, findings, and the like) provided in related exams or previous reports. Similarly, the reporting application 30 may be configured to access the order associated with the images, which may provide information regarding past exams, past findings or diagnoses, an anatomical structure, and patient conditions. Similarly, in some embodiments, the contextual information includes information obtained from a medical order associated with an image study. The medical order may be captured through a communication protocol, such as HL7, and may indicate what a reviewer is supposed to be reporting on in a study.

Furthermore, in some embodiments, the contextual information may include the reviewer's current or previous interactions with the reporting application 30 for the image study. For example, the contextual information may include an annotation (e.g., a measurement) being created by the reviewer on one or more images of the image study, a position of a cursor within the images, the reviewer's current focus on the images (e.g., using eye tracking), or a combination thereof. Similarly, the contextual information may include the workflow state of the reviewer within the reporting application 30. For example, the contextual information may include data elements previously selected by the reviewer (e.g., from a tree-structure of available discrete data elements or subsets thereof) and/or values previously provided by the reviewer for one or more of these data elements. The contextual information may also include information from prior studies. For example, if a prior study exists for a patient, the contextual information may include one or more data elements included in the report associated with the prior study. As described in more detail below, this contextual information may be used to include similar data elements in the report for the new study, data elements associated with sequential studies (e.g., tumor progression, location changes, etc.), or a combination thereof. Similarly, a location of a finding documented in a prior study may be used as contextual information that impacts data elements for the new study.

After determining the contextual information, the reporting application 30 uses the contextual information to perform one or more automatic actions. For example, as illustrated in FIG. 2, the reporting application 30 may automatically select at least one discrete data element for a structured report generated using the reporting application 30 for the image study based on the contextual information (at block 52). In particular, as one example, when the reviewer is reviewing an image of a heart, the reporting application 30 may use the contextual information to identify that a structured report for an image study of a heart typically includes discrete data elements providing findings for a left ventricle, a right ventricle, and an aorta. Therefore, the reporting application 30 may automatically identify a set of one or more potential discrete data elements for inclusion within the structured report. It should be understood that the one or more automatically-selected discrete data elements may include individual data elements, sets of related data elements that form a particular section of a structured report, or a combination thereof.

In some embodiments, the reporting application 30 displays a selected discrete data element to the reviewer and receives a selection from a reviewer indicating whether the reviewer wants to add or reject the data element (e.g., by receiving one or more selections from the reviewer). For example, in some embodiments, the reporting application 30 may be configured to automatically add an automatically selected discrete data element to the structured report, which the reviewer may reject (e.g., individually or as a set). Alternatively, the reporting application 30 may be configured to display an automatically selected data element to the reviewer and only add the data element to the structured report in response to the reviewer selecting or approving the data element for addition to the structured report.

In some embodiments, the reporting application 30 may also automatically prioritize the set of automatically selected discrete data elements (e.g., based on a determined probability of the data element being applicable based on the contextual information) and display the set of discrete data elements with priority information, such as in a prioritized order (from high priority to lowest priority) or with other indications designating what data elements are considered more probable (or important) than others. For example, the data elements with higher priority may be displayed in a particular format, such as color, size, font, etc. or displayed with an icon or other indicator. Also, in some embodiments, the reporting application 30 determines alternative options for discrete data elements (i.e., alternative discrete data elements), which the reporting application 30 may display to the reviewer for optional selection (e.g., approval or rejection).

In another example, the reporting application 30 may display an automatically selected discrete data element within a data structure (e.g., a tree structure) of available elements (without requiring that the reviewer navigate to the particular data element) and allow the reviewer to select the data element within the data structure or further navigate the data structure to select a different data element. Accordingly, in this situation, even if the reporting application 30 incorrectly identifies a data element for the structured report based on the contextual information, the reporting application 30 may eliminate interactions required by the reviewer to navigate a data structure of available data elements. The reporting application 30 may display automatically selected data elements in a different format (e.g., in a different color, size, font, format, etc.) than manually-selectable data elements within the data structure so that the reviewer may distinguish between automatically-selected data elements and data elements available for manual selection.

After automatically selecting the at least one discrete data element, the reporting application 30 receives a value for the at least one discrete data element (at block 54). In some embodiments, the reporting application 30 prompts the reviewer for a value, and the reviewer may provide the value by manually entering a value or selecting a value from a list of available values. Accordingly, the reporting application 30 may receive the value through an input mechanism of a user interface generated by the reporting application 30. Alternatively, a reviewer may provide the value through audio data (i.e., voice input). In these situations, the reporting application 30 may receive the audio data through interface with a microphone and use a natural language processing ("NLP") engine to process the audio data and generate corresponding text data for the data elements.

Also, in some embodiments, the reporting application 30 may receive the value from a piece of software automatically generating the value, or a combination thereof. For example, the reporting application 30 or a separate software application may be configured to automatically generate a value for a discrete data element (e.g., based on user selections of an image or a portion of an image). In embodiments where the value is automatically generated, the value may be displayed to a user to receive a user's approval or rejection.

As illustrated in FIG. 2, after receiving the value, the reporting application 30 adds the value for the at least one discrete data element to the structured report (at block 56). Accordingly, a reviewer may use the automatically selected data elements to build a structured report that satisfies the report requirements and preferences of the reviewer in an efficient manner that improves the performance of the reporting application 30.

In some embodiments, the reporting application 30 may also use the contextual information to automatically select other report parameters, such as annotation tools (e.g., measurement tools), display options, report formats, and the like applied by the reporting application 30. Also, the reporting application 30 may learn from reviewer interaction with automatically selected data elements to adjust selection criteria to learn specific report sections, reviewer preferences, and, in some situations, entire reports. For example, the reporting application 30 may identify automatically selected data elements that were previously (e.g., more than a predetermined threshold) rejected by one or a group of reviewers and may not select these data elements for future image studies. Similarly, in some situations, the reporting application 30 may be configured to automatically select an entire report template for an image study. Also, as noted above, information from prior studies (e.g., associated with the same patient) may be used to set up a framework for a report for a new study and may also be used to automatically identify relevant locations or areas within the new study (e.g., locations of tumors reported in previous studies).

In addition, in some embodiments, the reporting application 30 tracks the usage of particular data elements (e.g., a frequency of use across one or multiple reviewers) and uses the frequency of use along with the contextual information to automatically select data elements or other report parameters.

As illustrated in FIG. 2, alternatively or in addition to automatically selecting one or more data elements for a structured report, the reporting application 30 may automatically select a vocabulary for a natural language processing engine based on the contextual information (at block 60). The reporting application 30 also receives audio data from a reviewer interacting with the reporting application 30 (e.g., through an interface with a microphone) (at block 62) and processes the audio data with the natural language processing engine using the vocabulary to generate data for a report for the image study generated using the reporting application 30 (at block 64). For example, as noted above, in some embodiments, a reporting application 30 allows a reviewer to generate a report using free speech or allows a reviewer to provide values for a structured report using free speech. Accordingly, in these situations, the reporting application 30 uses a NLP engine to process audio data and generate textual report data. However, to provide better free speech processing, the reporting application 30 selects a particular vocabulary (e.g., limits a vocabulary of the NLP engine to a restricted set of terms and/or phrases) based on the contextual information. For example, when the contextual information indicates that the reviewer is generating a cardiology report, the NLP engine processes received audio data using only terms or phrases associated with cardiology. In this way, the NLP engine has a greater chance of understanding the semantics of free speech and identifying the appropriate values for a report.

Thus, embodiments of the invention provide systems and methods for using contextual information associated with images being reported on within a reporting application to generate a report. In particular, the contextual information allows a reporting application to narrow the number of report options to those that relate to the context of the report. For example, one method may include automatically selecting a vocabulary for a NLP engine based on contextual information available within a reporting application and using the selected vocabulary to process free speech representing a report or discrete data elements thereof. Another method may include automatically selecting one or more discrete data elements for a structured report based on contextual information available within a reporting application and optionally displaying the selected one or more discrete data elements to the reviewer for approval prior to adding the data elements to a structure report. As noted above, these methods may be performed independently or in combination. Also, the methods and systems described above may be used with other types of medical data, such as pathology reporting, EKG reporting, or other types of medical systems that provide data interpreted as a report. For example, sleep studies that report on breathing data, heart rates, oxygen saturation levels, leg movement data, and the like, may be generated using the methods and systems described above. Also, in some embodiments, the methods and systems described herein may be used to generated reports associated with non-medical data, such as geological data, aerial surveillance, and the like.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in computer readable storage medium with the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or server. In the later scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described here in with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

What is claimed is:

1. A method of generating reports for medical image studies, the method comprising:
   determining contextual information associated with a medical image study, the medical image study including a plurality of images generated as part of an imaging procedure, at least one image included in the medical image study loaded in a reporting application, wherein determining the contextual information includes processing the medical image study to determine at least one selected from a group consisting of a number of images included in the medical image study, header information for the at least one image, and a hanging protocol associated with the medical image study;

automatically selecting, with an electronic processor, a vocabulary for a natural language processing engine based on the contextual information;

receiving, from a microphone, audio data; and processing the audio data with the natural language processing engine using the vocabulary to generate data for a report for the medical image study generated using the reporting application, wherein the data for the report is displayed within the reporting application.

2. The method of claim 1, further comprising:

automatically selecting, with the electronic processor, one or more discrete data elements included in the report based on the contextual information; and prompting a reviewer for a value for each of the one or more discrete data elements.

3. The method of claim 2, further comprising prompting the reviewer to accept or reject each of the one or more discrete data elements.

4. The method of claim 1, wherein determining the contextual information further includes automatically identifying an anatomical structure represented in the at least one image and determining the contextual information based on the anatomical structure.

5. The method of claim 1, wherein determining the contextual information further includes determining at least one of an annotation created by a reviewer within the reporting application for the medical image study and a position of a cursor within the reporting application.

6. The method of claim 1 wherein determining the contextual information further includes determining a current focus of a reviewer within the at least one image displayed within the reporting application using eye tracking.

7. The method of claim 1, wherein determining the contextual information further includes accessing at least one of patient information for a patient associated with the medical image study and an order associated with the medical image study.

8. The method of claim 1, wherein determining the contextual information further includes determining at least one of a discrete data element previously selected by a reviewer for the report and a value previously specified by the reviewer for the report.

9. The method of claim 1, wherein processing the audio data with the natural language processing engine using the vocabulary to generate the data for the report includes processing the audio data to populate a data element of a structured report.

10. The method of claim 1, further comprising automatically select a report parameter for the report based on the contextual information, wherein the report parameter includes at least one selected from a group consisting of an annotation tool, a display option, and a report format.

11. A system for generating a structured report for a medical image study, the system comprising:

an electronic processor configured to:

determine contextual information associated with the medical image study, the medical image study including a plurality of images generated as part of an imaging procedure data and wherein the contextual information includes at least one selected from a group consisting of a number of images included in the medical image study, header information for at least one image included in the medical image study, and a hanging protocol associated with the medical image study;

automatically select a vocabulary for a natural language processing engine based on the contextual information;

receive audio data from a microphone; and process the audio data with the natural language processing engine using the vocabulary to generate the structured report for the data and display the structured report within a reporting application.

12. The system of claim 11, wherein the contextual information further includes an anatomical structure represented in the at least one image.

13. The system of claim 11, wherein the contextual information further includes at least one of patient information for a patient associated with the data and an order associated with the data.

14. Non-transitory computer-readable medium including instructions that, when executed by an electronic processor, perform a set of functions, the set of functions comprising:

determining contextual information associated with at least one image loaded in a reporting application, the at least one image included in a medical image study including a plurality of images and wherein the contextual information includes at least one selected from a group consisting of a number of images included in the medical image study, header information for the at least one image, and a hanging protocol associated with the medical image study;

automatically selecting a vocabulary for a natural language processing engine based on the contextual information;

receiving audio data; and processing the audio data with the natural language processing engine using the vocabulary to generate data for a report for the at least one image and displaying the data generated for the report using the reporting application.

15. The computer-readable medium of claim 14, wherein the report includes a structured report.

* * * * *